US012582568B2

(12) United States Patent
Pan et al.

(10) Patent No.: US 12,582,568 B2
(45) Date of Patent: Mar. 24, 2026

(54) ULTRASOUND-GUIDED INTERVENTIONAL OPERATION VEHICLE

(71) Applicant: FUWAI YUNNAN CARDIOVASCULAR HOSPITAL, Kunming (CN)

(72) Inventors: Xiangbin Pan, Beijing (CN); Shouzheng Wang, Beijing (CN); Zefu Li, Beijing (CN); Xiongjin Tan, Beijing (CN)

(73) Assignee: FUWAI YUNNAN CARDIOVASCULAR HOSPITAL, Kunming (CN)

( * ) Notice: Subject to any disclaimer, the term of this patent is extended or adjusted under 35 U.S.C. 154(b) by 635 days.

(21) Appl. No.: 18/122,883

(22) Filed: Mar. 17, 2023

(65) Prior Publication Data

US 2024/0238140 A1      Jul. 18, 2024

(30) Foreign Application Priority Data

Jan. 13, 2023     (CN) .......................... 202310066685.9

(51) Int. Cl.
A61G 12/00        (2006.01)
A61B 34/20        (2016.01)
(Continued)

(52) U.S. Cl.
CPC ............ A61G 12/001 (2013.01); A61B 34/20 (2016.02); A61M 19/00 (2013.01); B60H 3/0608 (2013.01);
(Continued)

(58) Field of Classification Search
CPC .................. A61G 12/001; A61B 34/20; A61B 2034/2063; A61M 19/00; B60H 3/0608; B60R 3/02; B60R 15/00; B62D 63/061
See application file for complete search history.

(56) References Cited

U.S. PATENT DOCUMENTS 4,181,347  A  *    1/1980  Clark ..................... A61G 3/001
                                                                 52/27
4,915,435  A  *    4/1990  Levine ................... A61G 3/001
                                                                 29/428
(Continued)

FOREIGN PATENT DOCUMENTS

WO      WO-2006053395 A1 *  5/2006  ................ B60P 3/14
WO      WO-2020218990 A1 * 10/2020  ................ B60P 3/36

*Primary Examiner* — Jacob B Meyer
(74) *Attorney, Agent, or Firm* — Scully, Scott, Murphy & Presser, P.C.

(57)                ABSTRACT
Provided is a vehicle for ultrasound-guided interventional operation, including: a vehicle body, wherein the vehicle body is provided with a carriage; an operating table arranged in the carriage; an operating lamp arranged in the carriage; an ultrasonic device arranged in the carriage, wherein the ultrasonic device is configured to provide the ultrasonic guidance; a monitoring device arranged in the carriage, wherein the monitoring device is configured to monitor vital signs of patients during the operation procedure; an anesthesia device arranged in the carriage, wherein the anesthesia device is configured to maintain an anesthesia state of the patient during the operation procedure; and a fixing device arranged on an inner wall of the carriage, wherein the fixing device is configured to fix the ultrasonic device, the monitoring device and the anesthesia device with the inner wall of the carriage during a driving process of the vehicle body.

20 Claims, 5 Drawing Sheets

(51) Int. Cl.

| | |
|---|---|
| *A61M 19/00* | (2006.01) |
| *B60H 3/06* | (2006.01) |
| *B60R 3/02* | (2006.01) |
| *B60R 15/00* | (2006.01) |
| *B62D 63/06* | (2006.01) |

(52) U.S. Cl.

CPC ................ *B60R 3/02* (2013.01); *B60R 15/00* (2013.01); *B62D 63/061* (2013.01); *A61B 2034/2063* (2016.02)

(56) References Cited

U.S. PATENT DOCUMENTS

| | | | | |
|---|---|---|---|---|
| 5,775,758 | A * | 7/1998 | Eberspacher | B60P 3/14 296/19 |
| 6,039,377 | A * | 3/2000 | Eberspacher | A61G 3/001 296/19 |
| 6,082,799 | A * | 7/2000 | Marek | B60P 3/14 296/19 |
| 6,481,887 | B1 * | 11/2002 | Mirabella | A61B 6/563 378/198 |
| 7,347,472 | B2 * | 3/2008 | Pellegrin, Jr. | G09B 23/28 434/262 |
| 8,221,684 | B2 * | 7/2012 | Sukumar | B60P 3/14 422/65 |
| 8,888,495 | B2 * | 11/2014 | Johnson | G09B 5/06 434/219 |
| 8,919,849 | B1 * | 12/2014 | Robertson | A61B 6/4441 296/24.38 |
| 9,308,141 | B2 * | 4/2016 | Blackwell | B60P 3/14 |
| 9,334,664 | B2 * | 5/2016 | Wall | A61G 12/00 |
| 9,802,655 | B2 * | 10/2017 | Sharbono | A61G 3/00 |
| 10,213,351 | B2 * | 2/2019 | Thompson | A61G 3/001 |
| 10,307,313 | B2 * | 6/2019 | Schroeder | F16M 11/2078 |
| 10,398,207 | B2 * | 9/2019 | Schroeder | A45C 13/1069 |
| 2003/0060808 | A1 * | 3/2003 | Wilk | A61G 3/001 606/1 |
| 2024/0238140 | A1 * | 7/2024 | Pan | A61G 12/001 |

* cited by examiner

ULTRASOUND-GUIDED INTERVENTIONAL OPERATION VEHICLE

CROSS-REFERENCE TO RELATED APPLICATION

This application claims the priority of Chinese Patent Application No. 202310066685.9 filed on Jan. 13, 2023 in the China National Intellectual Property Administration, the content of which is incorporated herein by reference in entirety.

TECHNICAL FIELD

The present disclosure relates to a field of medical equipment technology, and in particular, to a vehicle for ultrasound-guided interventional operation.

BACKGROUND

Interventional operation is a commonly used minimally invasive diagnosis and treatment method, which is required to be conducted under the guidance of medical imaging equipment, such as an X-ray radiography equipment or an ultrasonic device. In some cases, it is of great necessity to perform the interventional operation at other places other than a hospital. Therefore, there is an urgent requirement for an operation vehicle that may be facilitated for interventional operation.

SUMMARY

In view of the above-mentioned problem, the present disclosure is developed to provide an ultrasound-guided interventional operation vehicle to overcome the above-mentioned problem or at least partially solve the above-mentioned problem.

Embodiments of the present disclosure provide a vehicle for ultrasound-guided interventional operations, including: a vehicle body, wherein the vehicle body is provided with a carriage; an operating table arranged in the carriage; an operating lamp arranged in the carriage; an ultrasonic device arranged in the carriage, wherein the ultrasonic device is configured to provide the ultrasonic guidance; a monitoring device arranged in the carriage, wherein the monitoring device is configured to monitor vital signs of patients during an operation procedure; an anesthesia device arranged in the carriage, wherein the anesthesia device is configured to maintain an anesthesia state of the patient during the operation procedure; and a fixing device arranged on an inner wall of the carriage, wherein the fixing device is configured to fix the ultrasonic device, the monitoring device and the anesthesia device with the inner wall of the carriage during a driving process of the vehicle body.

DETAILED DESCRIPTION OF EMBODIMENTS

In order to make objectives, technical solutions and advantages of embodiments of the present disclosure more clear, technical solutions in embodiments of the present disclosure will be described clearly and completely with reference to the accompanying drawings. It is obvious that embodiments described are only some embodiments of the present disclosure, rather than all embodiments. All other embodiments, which may be derived by those of ordinary skill in the art from embodiments in the present disclosure without creative labor, are intended to be within the scope of the present disclosure.

Interventional operation is required to be completed under a guidance of medical imaging equipment. Common guidance equipment includes the ultrasound device, the X-ray radiological equipment, and the like. Compared with X-ray guidance, the ultrasound guidance takes advance in free of radiation and less requirements for the on-site operation. Therefore, in the embodiment, the equipment required for ultrasound-guided interventional operation is selected to be arranged in the vehicle to complete the interventional operation in other places outside the hospital.

The ultrasound-guided interventional operation vehicle provided in embodiments of the present disclosure integrates a full set of equipments required for ultrasound-guided interventional operation on the vehicle, so that the interventional operation may be completed at any required place, in the meantime, the safety of all equipment may be ensured during the driving process of the vehicle.

Figure 1:
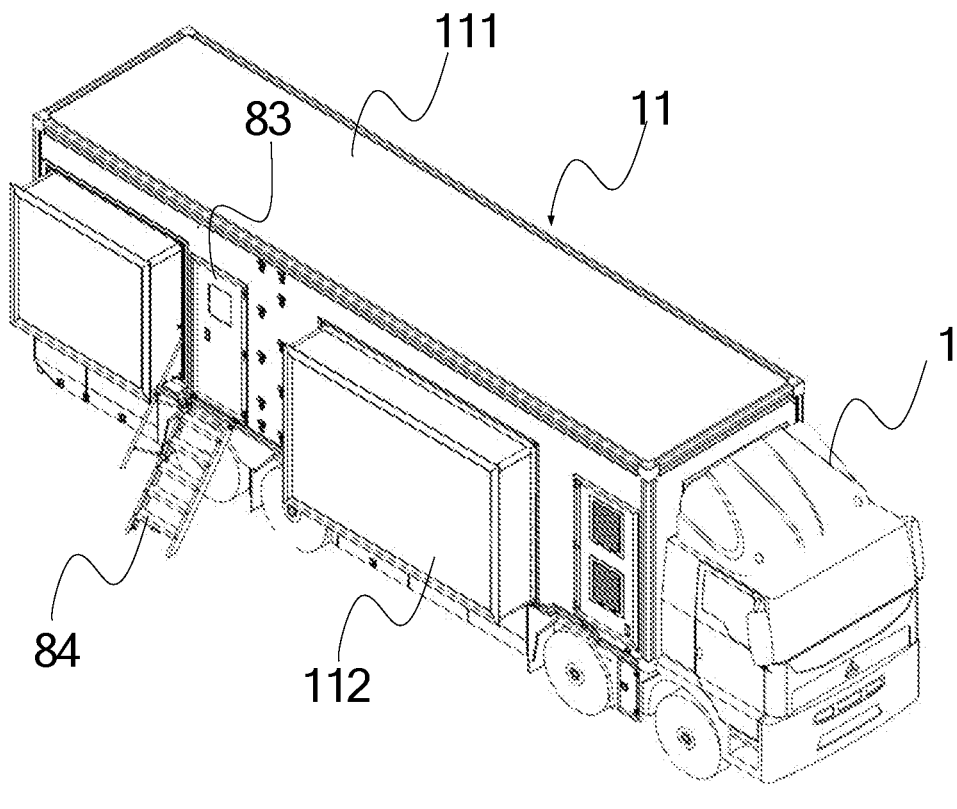
FIG. 1 shows a schematic isometric view of an ultrasound-guided interventional operation vehicle provided in embodiments of the present disclosure.
Figure 2:
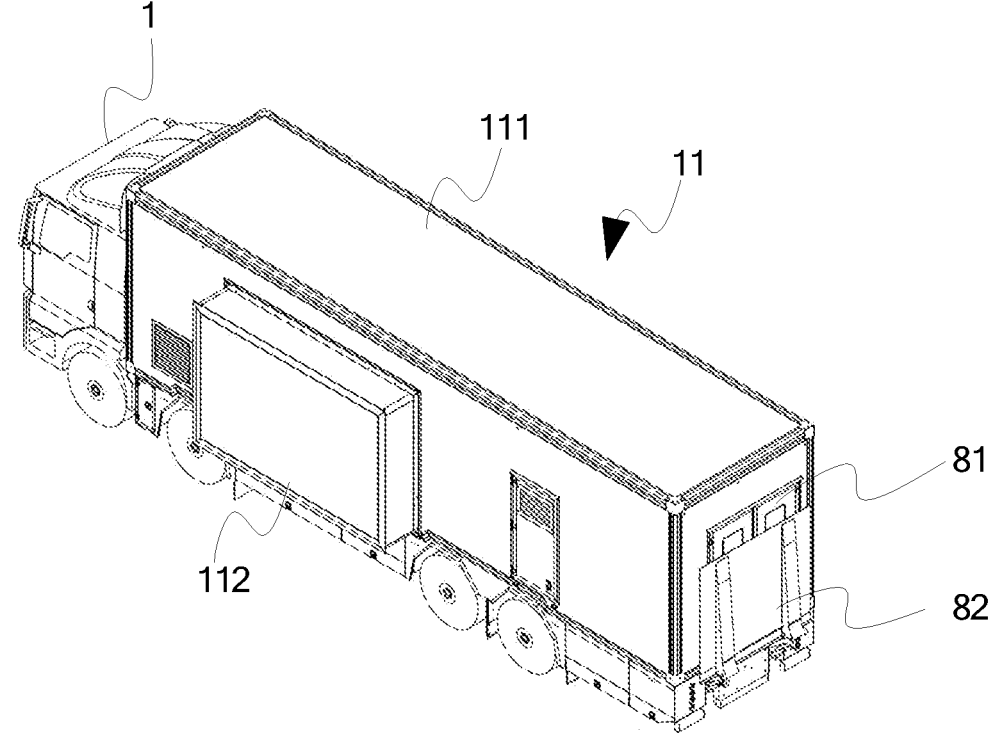
FIG. 2 shows another schematic isometric view of an ultrasound-guided interventional operation vehicle provided in embodiments of the present disclosure.
Figure 3:
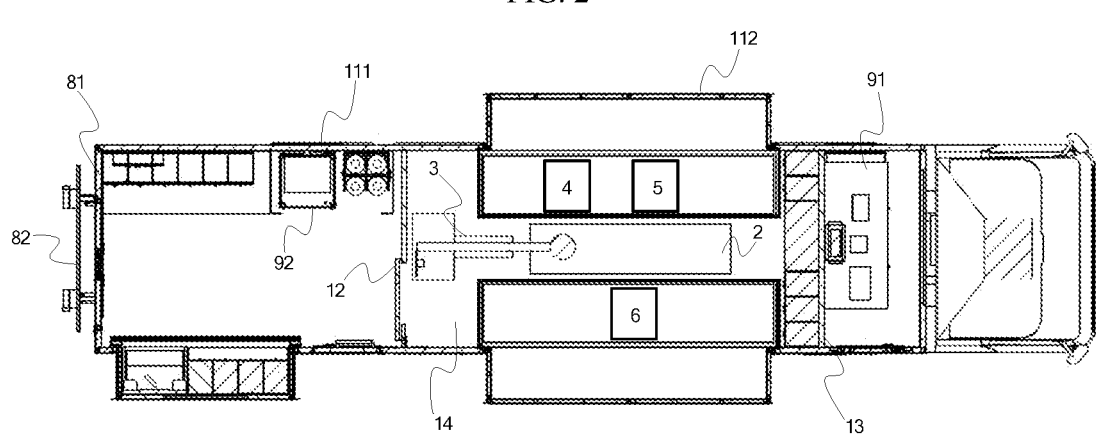
FIG. 3 shows an internal structure diagram of the ultrasound-guided interventional operation vehicle according to embodiments of the present disclosure.
Figure 4:
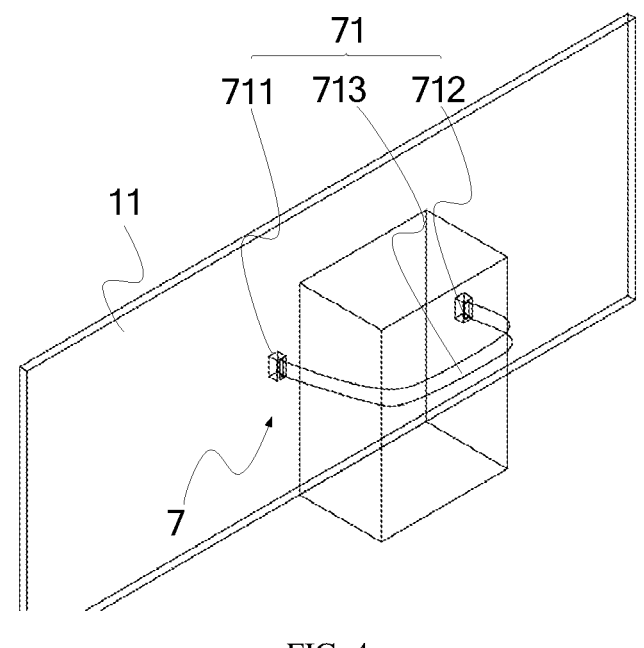
FIG. 4 shows a schematic diagram of a fixing device according to an embodiment of the present disclosure.

FIG. 1 shows a schematic isometric view of an ultrasound-guided interventional operation vehicle provided in embodiments of the present disclosure. FIG. 2 shows another schematic isometric view of an ultrasound-guided interventional operation vehicle provided in embodiments of the present disclosure. FIG. 3 shows an internal structure diagram of the ultrasound-guided interventional operation vehicle according to embodiments of the present disclosure. FIG. 4 shows a schematic diagram of a fixing device according to an embodiment of the present disclosure. Referring to FIG. 1 to FIG. 4, embodiments of the present disclosure provide an ultrasound-guided interventional operation vehicle, including: a vehicle body 1, an operating table 2, an operating lamp 3, an ultrasonic device 4, a monitoring device 5, an anesthesia device 6, and a fixing device 7.

The vehicle body 1 may be a trailer vehicle and any other vehicle with suitable specifications provided in the relevant technology in the art, and the vehicle body 1 is provided with a carriage 11. Detailed specifications of the carriage 11 may be selected according to the actual needs, and there is no limitation on this. The carriage 11 may be a device such as a container. The carriage 11 may be provided with a thermal insulation layer, a waterproof layer and other structures to ensure a stability of an environment inside the carriage 11. Those skilled in the art may reasonably set a specific structure of the carriage 11 according to a specific use environment of the ultrasound-guided interventional operation vehicle, and there is no limitation on this.

The operating table 2 and the operating lamp 3 are arranged in the carriage 11. The operating table 2 is used to place a patient during an interventional operation. The operating table 2 may have a lifting function to facilitate an adjustment of the patient to a suitable height for operation during the interventional procedure. A bottom of the operating table 2 may be fixedly connected with a bottom plate of the carriage 11 by welding and other ways to prevent the operating table 2 from sliding during the driving of the vehicle body 1. Alternatively, the bottom of the operating table 2 may be slidably connected with the bottom plate of the carriage 11. For example, in some embodiments, the bottom plate of the carriage 11 may be provided with a slide rail, while a bottom foot of the operating table 2 may be slidably arranged in the slide rail to facilitate an adjustment of a position of the operating table 2. At the same time, the slide rail may be provided with a locking structure to avoid a sliding of the operating table 2 during the driving process of the vehicle body 1 or during the interventional operation. Those skilled in the art may make a selection according to the actual needs, and there is no limitation on this.

The operating lamp 3 may be used for lighting during the interventional operation. The operating lamp 3 may be connected with a top plate of the carriage 11 and configured to move relative to the top plate of the carriage 11, so that the operating lamp 3 may be adjusted to an appropriate position for lighting during the interventional operation. Alternatively, the operating lamp 3 may be fixed on a movable bracket in order to adjusted the operating lamp 3 to an appropriate position for lighting during the interventional operation. Several specific structures of the operating lamp 3 will be provided further in the relevant parts below, which will not be repeated here.

The ultrasonic device 4, the monitoring device 5, the anesthesia device 6, etc. are also arranged in the carriage 11. The ultrasonic device 4 is used to provide an ultrasonic guidance during the interventional operation, the monitoring device 5 is used to monitor vital signs of patients during the interventional operation, and the anesthesia device 6 is used to maintain an anesthesia state of the patient during the operation procedure.

The ultrasonic device 4 may be a common ultrasonic machine in the art. The bottom of the ultrasonic device 4 may be provided with a wheel to enable the ultrasonic device 4 to be adjusted to an appropriate position during the interventional operation. The monitoring device 5 may include respiratory monitoring equipment, ECG monitoring equipment and other monitoring equipments that need to be used in interventional operation. The monitoring device 5 may be positioned on a movable bracket to enable the monitoring device 5 to be adjusted to an appropriate position during the interventional operation. The anesthesia device 6 may include an infusion stand, an automatic injection device and other equipment used for injecting anesthetic drugs, and a ventilator and other equipment used for assisting respiration. Similarly, the bottom of the above equipment may be provided with a wheel, or the above equipment may be arranged on the movable bracket.

The fixing device 7 is arranged on an inner wall of the carriage 11. As described above, the ultrasonic device 4, the monitoring device 5, the anesthesia device 6, etc., all have a function of moving, rather than being fixed on the bottom plate of the carriage 11. Therefore, during the driving process of the vehicle body 1, the above-mentioned devices may move and cause accidental collision. Therefore, in the embodiment, the fixing device 7 is provided to fix the above-mentioned devices with the inner wall of the carriage 11 during the driving of the vehicle body 1. The fixing device 7 may be any structure that is capable of being connected to and fixing the above-mentioned devices. Several arrangement modes of the fixing device will be described in detail below, which will not be repeated here. The inner wall here may refer to an inner side wall of the carriage 11 and an inner bottom wall of the carriage 11.

In addition to the above-mentioned devices, the carriage 11 may also be provided with other devices required for the interventional operation, such as a storage rack for placing an operating instrument, an infusion rack for blood transfusion, and a suction device for suction. These devices may also be set to be movable, and the above-mentioned fixing device 7 may also be used to fix these devices.

Generally, it is understandable that although ultrasound guidance is used to conduct the interventional operation in the embodiment, using X-ray imaging device to physically examine a patient prior to an initiation of the interventional operation is helpful for ultrasound-guided curative treatment to locate more accurately. For this reason, in some embodiments, an X-ray imaging device may be arranged in the carriage 11, and since the X-ray imaging device is only used for physical examination and not for guidance during the interventional operation, a requirement for radioactive shielding is scarce. The radioactive shielding requirement may be achieved via providing a lead plate or other radioactive shielding structures on each wall of the carriage 11.

In actual use, devices are specifically arranged in the carriage 11 and may be selected according to a specific use requirement. In some embodiments, the ultrasound-guided interventional operation vehicle may have different versions, such as a standard version and an advanced version. Compared with the standard version, the carriage 11 of the advanced version of the ultrasound-guided interventional operation vehicle may be configured with more devices and/or more advanced devices.

In some embodiments, the fixing device 7 may include a plurality of fixing pieces 71, and each of the fixing pieces 71 corresponds to a to-be-fixed device. The to-be-fixed device here may refer to one of the ultrasonic device 4, the monitoring device 5, the anesthesia device 6 and other devices described above that need to be fixed during the driving of the vehicle body 1. In the embodiment, each to-be-fixed device is fixed independently, thus further avoiding the collision between these to-be-fixed devices. In some embodiments, the fixing pieces 71 may be respectively arranged on different inner walls of the carriage 11 to further optimize a layout of various to-be-fixed devices.

In some embodiments, specifically, referring to FIG. 4, each fixing piece 71 may include: a first fixing part 711, a second fixing part 712 and a fixing belt 713. The first fixing part 711 and the second fixing part 712 are arranged on an inner side wall of the carriage 11, and two ends of the fixing belt 713 are respectively connected with the first fixing part 711 and the second fixing part 712, so that the fixing belt 713 may fix the to-be-fixed device in an accommodation space formed between the fixing belt 713 and the inner wall of the carriage 11.

In the embodiment, the fixing belt 713 is used to fix the to-be-fixed device, which has advantages that a contact area between the fixing belt 713 and the to-be-fixed device is adequate, so as to avoid the to-be-fixed device from being damaged due to over-large local stress while having better fixing effect.

In some embodiments, a distance between the first fixing part 711 and the second fixing part 712, and a length of the fixing belt 713 may be adapted to the corresponding to-be-fixed device. A connection between the fixing belt 713 and the first fixing part 711 and/or the second fixing part 712 may be detachable. In actual use, one or two ends of the fixing belt 713 may be detached, and then the to-be-fixed device may be attached with or without.

In some embodiments, each fixing piece 71 may further include an accommodating part (not shown in the figures), which is rotatably arranged in the first fixing part 711, and an end portion of the fixing belt 713 may be fixedly connected with the accommodating part. When the accommodating part rotates, the fixing belt 713 may be accommodated in the first fixing part 711, or released from the first fixing part 711.

In the embodiment, a length of the fixing belt 713 may be adjusted by rotating the accommodating part to make the fixing belt 713 more stably fix the to-be-fixed device.

In some embodiments, the accommodating part may be configured to automatically rotate under an action of a preload spring. When the fixing belt 713 is not subjected to a sufficient force, the accommodating part may automatically rotate to accommodate the fixing belt 713 into the first fixing part 711. In the embodiment, the automatic accommodating of the fixing belt 713 is realized, which simplifies operation steps when fixing the to-be-fixed device.

In some embodiments, an accommodating part may further be provided in the second fixing part 712.

In some embodiments, each fixing piece 71 further includes a stopping part which is connected with the accommodating part. The stopping part in the embodiment may limit a rotation of the accommodating part, so as to fix the fixing belt 713 at a suitable length, so that the fixing belt 713 may perform a good fixing function.

In some embodiments, the stopping part is configured to automatically limit the rotation of the accommodating part when the fixing belt 713 is subjected to a force greater than a preset value. In the embodiment, when the fixing belt 713 is subjected to a light force, for example, when the operator manually stretches, the accommodating part may rotate freely, and when the fixing belt 713 is subjected to a huge force, for example, when the fixed device shakes violently, the stopping part may automatically limit the rotation of the accommodating part, so that the fixing belt 713 will not be relaxed. In the embodiment, it is not necessary to manually operate the stopping part to limit the rotation of the accommodating part, which further simplifies the operation.

Figure 5:
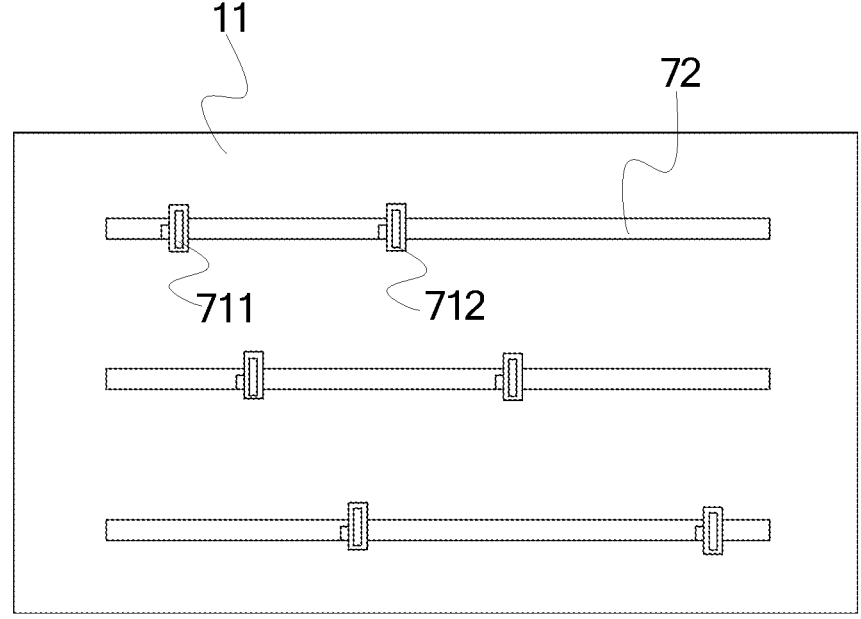
FIG. 5 shows a schematic diagram of a fixing device according to another embodiment of the present disclosure.

FIG. 5 shows a schematic diagram of a fixing device according to another embodiment of the present disclosure. In some embodiments, the fixing device 7 further includes a guide rail 72, and the guide rail 72 is arranged on an inner side wall of the carriage 11. The first fixing part 711 and the second fixing part 712 are slidably connected with the guide rail 72. In the embodiment, positions of the first fixing part 711 and the second fixing part 712 may be adjusted by sliding, so that the first fixing part 711 and the second fixing part 712 may adapt to the to-be-fixed devices in different specifications and has more flexibility in application.

In some embodiments, the fixing device 7 may include a plurality of guide rails 72, and the plurality of guide rails 72 are arranged at different heights of the inner side wall of the carriage 11. The arrangement of the plurality of guide rails 72 with different heights may better meet fixation require-ments of to-be-fixed devices with different specifications, so that the fixing belt 713 may be close to a center of gravity of the to-be-fixed device, so as to have a better fixation effect. In some embodiments, the plurality of guide rails 72 may also be respectively arranged on different inner side walls of the carriage 11.

Figures 6, 7:
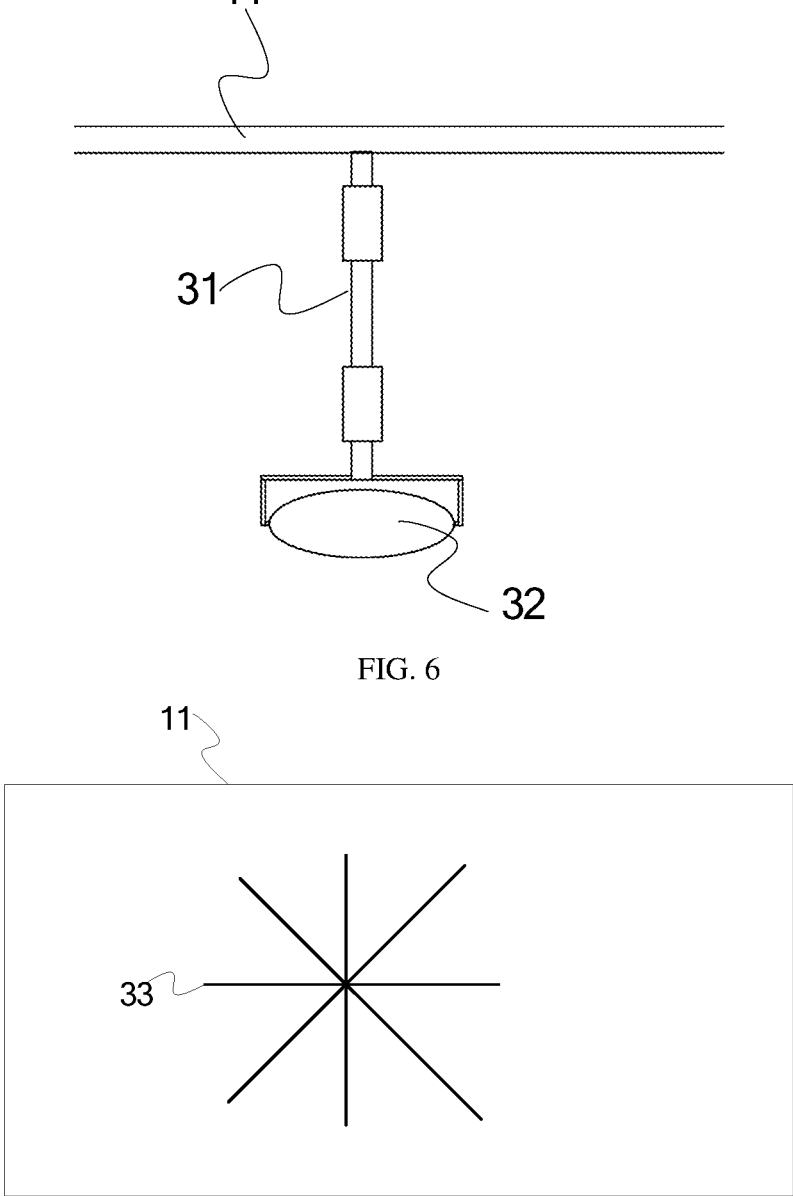
FIG. 6 shows a schematic diagram of an operating lamp according to an embodiment of the present disclosure.
FIG. 7 shows a schematic diagram of a chute according to an embodiment of the present disclosure.

FIG. 6 shows a schematic diagram of an operating lamp according to an embodiment of the present disclosure. In some embodiments, the operating lamp 3 may include a telescopic part 31 and a lamp cap 32. The telescopic part 31 is slidably connected with a top plate of the carriage 11, so that a position of the lamp cap 32 may be adjusted when the telescopic part 31 slides, and the telescopic part 31 extends towards a bottom plate of the carriage 11, so that a height of the lamp cap 32 may be adjusted when the telescopic part 31 expands and contracts, and the lamp cap 32 may be rotatably arranged at an end of the telescopic part 31 close to the bottom plate of the carriage 11, so that an angle of the lamp cap 32 may be adjusted by rotating the lamp cap 32.

In the embodiment, the telescopic part 31 may be a telescopic rod-shaped structure, for example, the telescopic part 31 may include two or more slidably connected sleeve structures. The lamp cap 32 may be a common shadowless lamp in the art. A rotating connection between the lamp cap 32 and the telescopic part 31 may be realized by a universal head, or by a bearing. When the rotating connection is realized by the bearing, it may be necessary to set up a plurality of bearings on different rotating axes to meet a multi-angle rotation of the lamp cap 32.

It may be understood that the operating lamp provided in the relevant technology in the art is generally a structure configured with two or more rocker arms, which are rotated and connected in turn, and the lamp cap is connected to the lowest rocker arm, so as to realize the movement of the lamp cap on a plurality of degrees of freedom.

However, different from the conventional operating room, the vehicle has a height limit requirement, thus a height of the top plate of the carriage 11 is limited, and it is extremely inconvenient to adjust the operating lamp provided with a plurality of rocker arms in such a carriage 11. Therefore, in the embodiment, a movement of the lamp cap 32 in a plurality of degrees of freedom may be achieved by a sliding between the telescopic part 31 and the top plate of the carriage 11, an expansion and contraction of the telescopic part 31, and a rotation between the lamp cap 32 and the telescopic part 31. Compared with the operating lamp pro-vided with a plurality of rocker arms, the operating lamp 3 in the embodiment occupies less space in a vertical direc-tion, which is convenient for use in an environment with a low top plate height such as the carriage 11.

FIG. 7 shows a schematic diagram of a chute according to an embodiment of the present disclosure. In some embodi-ments, the top plate of the carriage 11 is provided with a chute 33, and an end of the telescopic part 31 is slidably arranged in the chute 33 to realize a sliding connection between the telescopic part 31 and the top plate of the carriage 11.

In some embodiments, still referring to FIG. 7, the roof plate of the carriage 11 may be provided with a plurality of chutes 33, and the plurality of chutes 33 are arranged radially, and the telescopic part 31 may slide in any one of the chutes 33. In the embodiment, the telescopic part 31 may slide in a larger range and in more directions by providing a plurality of radially arranged chutes 33, so that the position of the lamp cap 73 may be adjusted more flexibly.

Figure 8:
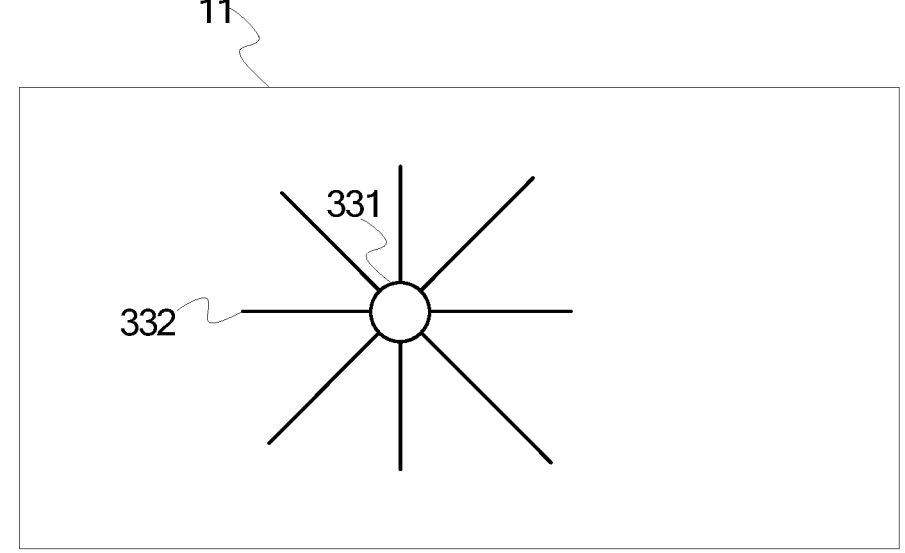
FIG. 8 shows a schematic diagram of a chute according to another embodiment of the present disclosure.

FIG. 8 shows a schematic diagram of a chute according to another embodiment of the present disclosure. In some embodiments, the chute 33 may include a circular chute 331 and a plurality of linear chutes 332. The plurality of linear chutes 332 are connected with the circular chute 331 and arranged radially around the circular chute 331. The telescopic part 31 may slide in the circular chute 331 or any one of the linear chutes 332.

In the embodiment, the moving range and direction of the telescopic part 31 are still expanded by providing a plurality of radially arranged linear chutes 332, except that, in the embodiment, the circular chute 331 is further arranged in the center of the plurality of linear chutes 332, thus, during an actual changing-direction process, the telescopic part 31 may be slid from the linear chute 332 to the circular chute 331, and then from the circular chute 331 to a next linear chute 332, so that the operation may be smoother, and it is not required to consume a large amount of time to complete an alignment operation between the chutes.

In some embodiments, still referring to FIG. 1 and FIG. 2, the carriage 11 may include a main carriage 111 and at least one expansion carriage 112. The expansion carriage 112 is slidably connected with a side wall of the main carriage 111, so that the expansion carriage 112 may be accommodated in the main carriage 111 or slid out of the main carriage 111 to expand a space.

It may be understandable that the vehicle has not only a height limit requirement, but also a width limit requirement, and for this reason, in the embodiment, the expansion carriage 112 is provided to expand the space. During the driving process of the vehicle body 1, the expansion carriage 112 may be accommodated in the main carriage 111, and after the vehicle body 1 arrives at a destination, the expansion carriage 112 may be slid out to realize the space expansion. As an example, each of two side walls of the main vehicle 111 may be provided with one expansion carriage 112.

In some embodiments, specifically, each expansion carriage 112 may specifically include: a side plate 1121 and a main plate 1122. Specifically, the expansion carriage 112 includes four side plates 1121, which are upper side plate, lower side plate, left-side plate and right-side plate. The four side plates 1121 are slidably connected with the side wall of the main carriage 111, and the main plate 1122 is rotatably connected with the side panels 1121. When the expansion carriage 112 is accommodated into the main carriage 111, the side panels 1121 may be fitted with an inner surface of the side wall of the main carriage 111. In the embodiment, a rotating connection between the side panels 1121 and the main plate 1122 enables the side panels 1121 to be fitted with the inner surface of the side wall of the main carriage 111 after being accommodated into the main carriage 111, thus avoiding the side panels 1121 occupying a space inside the main carriage 111 when the side panels 1121 being accommodated.

In some embodiments, a joint between the side plates 1121 and the main carriage 111 may be provided with a sealing strip. Of note, it may be understandable that due to a sliding connection between the side panels 1121 and the main carriage 111, there is a certain gap between the side panels 1121 and the main carriage 111, which may cause dust in the external environment to enter an interior of the carriage 11, thus to some extent, affecting a cleanness of an operating environment. Therefore, in the embodiment, the sealing strip is further provided at the joint between the side panels 1121 and the main carriage 111 to avoid the occurrence of the above-mentioned situation.

In some embodiments, the bottom of the carriage 11 may be provided with a supporting structure. It may be understandable that a stability of the carriage 11 and a level of the carriage 11 are required to be guaranteed during the operation procedure. However, the level and stability of the carriage 11 may not be fully guaranteed by the wheel of the vehicle body 1, thus, in the embodiment, the supporting structure is further provided at the bottom of the carriage 11, and the supporting structure may be in a retracted state during the driving process of the vehicle to avoid interfering with a normal driving of the vehicle, and the supporting structure may be unfolded and supported on the ground during the operation procedure to maintain the level and stability of the carriage 11. In some embodiments, if the expansion carriage 112 is provided, the above-mentioned supporting structure may be arranged at the bottom of the main carriage 111 and at the bottom of the expansion carriage 112.

Figure 9:
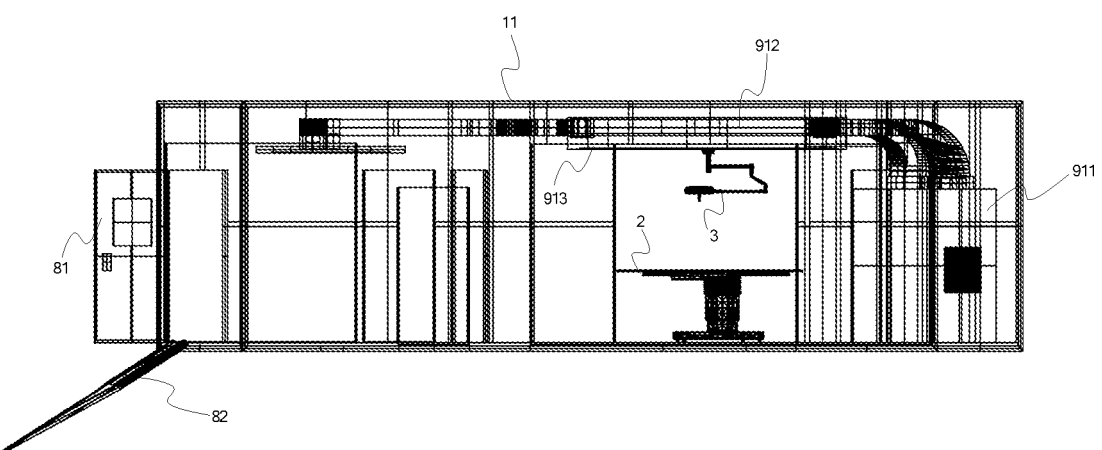
FIG. 9 shows a perspective view of an ultrasound-guided interventional operation vehicle according to embodiments of the present disclosure.

FIG. 9 shows a perspective view of an ultrasound-guided interventional operation vehicle according to embodiments of the present disclosure. In some embodiments, referring to FIG. 2 and FIG. 9, the ultrasound-guided interventional operation vehicle further includes: a transfer door 81 and a transfer ladder 82. The transfer door 81 is arranged at a rear of the carriage 11, and the transfer ladder 82 is also arranged at the rear of the carriage 11 and rotatably connected with a bottom plate of the carriage 11. When it is not necessary to transfer a patient, referring to FIG. 2, the transfer ladder 82 may be rotated to a state roughly parallel to the transfer door 81 and covered on an outer surface of the transfer door 81. When it is necessary to transfer a patient, the other end of the transfer ladder 82 may be abutted on the ground by rotating the transfer ladder 82, thus forming a slope as shown in FIG. 9.

In the embodiment, not only the transfer door 81 is provided, but also the transfer ladder 82 is provided, which makes a transfer of patient more convenient.

In some embodiments, the transfer ladder 82 may include a plate body, a track and a driving part (not shown in the figures). An end of the plate body may be rotatably connected with the bottom plate of the carriage 11. The track is covered on a surface of the plate body. The track may be provided with structures such as patterns and the like which may increase a frictional force. The driving part may drive the track to slide relative to the plate body, thus a patient standing on the track may be driven to move by the sliding of the track and the friction provided by the track. In the embodiment, the transfer ladder 82 may be more convenient for the transfer of patient, especially for a patient with compromised mobility.

In some embodiments, a foldable handrail may be arranged on two sides of the plate body. When the transfer ladder is unfolded, the handrail on two sides of the plate body may also be unfolded. The patient and other personnel may hold the handrail to complete the transfer, thus ensuring a safety of a transfer process.

In some embodiments, the patient may sit on a wheelchair or lie on a transfer bed during the transfer process, and a wheel is arranged at the bottom of the wheelchair and the bottom of the transfer bed. For this reason, the track may be further provided with two butting parts, and the two butting parts may be butted on the two wheels behind the wheelchair or transfer bed to avoid accidental sliding of the wheelchair or transfer bed during the transfer process.

In other embodiments, the transfer ladder may include a plate body and a hydraulic supporting part. An end of the plate body is rotatably connected with the bottom plate of the carriage 11, while the hydraulic supporting part is arranged at an end of the plate body away from the carriage 11. When the plate body is unfolded, the hydraulic supporting part may be butted on the ground, and then the hydraulic supporting part may support the plate body to rotate upward until the plate body reaches a state close to parallel with the ground. Compared with the transfer ladder provided with the track, a structure of the transfer ladder in the embodiment is simpler, but may cause a large shaking during the transfer process, and a safety performance is relatively poor.

In some embodiments, referring to FIG. 1, a side of the carriage 11 may be provided with a second transfer door 83 and a second boarding ladder 84, and the second transfer door 83 and the second boarding ladder 84 may be used for other medical personnel to enter and exit the carriage 11. Since the medical personnel's mobility is not limited, the second boarding ladder 84 may be a simple ladder without a need to configure a power assist structure.

In some embodiments, referring to FIG. 3, the carriage 11 may be provided with an isolation door 12 and an isolation plate 13. The isolation door 12, the isolation plate 13 and the side wall of the carriage 11 jointly define an operating room 14, and the isolation door 12 is arranged on a side close to the rear of the carriage 11. In the embodiment, an internal space of the carriage 11 is further functionally divided, and a relatively independent and closed operating room 14 is formed to ensure a safety of an operating environment.

The isolation door 12 may be an infrared sensing automatic door, which may be opened automatically when sensing a presence of an object in front of the door. Alternatively, the isolation door 12 may be a tactile automatic door, and the bottom of the isolation door 12 may be provided with a tactile switch. The medical staff may step on the tactile switch to open the automatic door, so as to prevent the medical staff from contaminating their hands.

A space between the isolation door 12 and the transfer door 81 may be used as a preparation room, where the medical staff may complete a preparation work before entering the operating room 14. For example, in some embodiments, there may be provided a washing table, where the medical staff may complete a hand disinfection work. In some embodiments, an oxygen cylinder and other items required for the operation but not suitable for placing in the operating room 14 may also be arranged here.

In some embodiments, the expansion carriage 112 may be arranged in a corresponding region of the operating room 14 and a corresponding region of the preparation room, respectively.

In some embodiments, a plurality of storage cabinets may be provided on a side of the isolation plate 13 close to the operating room 14, and the plurality of storage cabinets may be used to store an operating instrument, an operating consumable, and the like. In some embodiments, the side of the isolation plate 13 close to the operating room 14 may be further provided with an intelligent terminal, and the intelligent terminal may be used for communication, operating video recording, equipment control in the operating room 14 and other functions.

A space between the isolation plate 13 and a head of the carriage 11 may be set up as an equipment room, where some large equipment, such as some electrical equipment, may be placed. In some embodiments, the equipment room may be provided with an on-board battery to supply power to each equipment on the vehicle. In some embodiments, power supply sources of each equipment on the vehicle may be various. In addition to the on-board battery, an internal combustion engine of the vehicle body 1 may also be used for power supply, or a solar panel arranged on the top of the vehicle may be used for power supply, or an external power supply may be used for power supply, to avoid an accident due to a depletion of power during the operation procedure.

In some embodiments, the ultrasound-guided interventional operation vehicle further includes an air purification device 91, and the air purification device 91 is used to purify the air in the operating room 14. The air purification device 91 may be a common laminar flow purification system in the art, and the laminar flow purification system may purify the air in the operating room 14, so that the environment in the operating room 14 may meet a requirement of asepsis.

In some embodiments, specifically, referring to FIG. 9, the air purification device 91 may include an air purifier 911, an air duct 912, and a plurality of air outlets 913. The air purifier 911 is arranged on a side of the isolation plate 13 away from the operating room 14. i.e., arranged in the equipment room described above. The air duct 912 is connected with the air purifier 911. The air duct 912 passes through the isolation plate 13 and extends at a top of the operating room 14. The plurality of air outlets 913 are arranged on a side of the air duct 912 facing a bottom of the operating room 14. In the embodiment, the plurality of air outlets 913 are actually arranged on the top of the operating room 14, thus forming a top-down airflow in the operating room 14 to achieve better purification effect. In some embodiments, the air duct 912 may be extended in a square shape at the top of the operating room 14, so that the plurality of air outlets 913 may cover a larger area.

In some embodiments, the air duct 912 may further pass through the isolation door 12 and extend into the preparation room described above to purify the air in the preparation room.

In some embodiments, the air duct 912 may be further provided with a filter to secondarily purify the air flowing out of the air purifier 911 to achieve better purification effect. In some embodiments, the air duct 912 may be provided with a silencing device. For example, a surface of the air duct 912 may be coated with a mute cotton to avoid large noise during an operation of the air purification device 91. In some embodiments, the air purifier 911 may have a temperature regulation function, which enables the air purification device 91 to maintain a temperature in the operating room 14 in a suitable range while purifying the air in the operating room 14. In some embodiments, a size of the air outlet 913 may be adjusted to change a gas flow.

In some embodiments, the air purification device 91 may further include an air return duct connected to the air purifier 911. The air return duct may also extend to the operating room 14. A gas circulation in the operating room 14 may be accelerated by providing the air return duct. In some embodiments, a fresh air outlet may be formed on a side wall of the equipment room to introduce fresh air into the air purification device 91.

In some embodiments, referring to FIG. 3, the ultrasound-guided interventional operation vehicle further includes a waste treatment device 92, and the waste treatment device 92 is arranged on a side of the isolation door 12 away from the operating room 14, i.e., arranged in the preparation room described above. The waste treatment device 92 is used to treat the medical waste generated during the operation procedure.

As an example, the waste treatment device 92 may include a vacuum compression part and a storage part, and the vacuum compression part is used to perform a vacuum and compression treatment on the medical waste, while the storage part is used to store the treated medical waste.

It may be understood that, unlike a hospital where there is a dedicated waste treatment area, a working environment of the ultrasound-guided interventional operation vehicle is not provided with a medical waste treatment area, and the medical waste may not be discarded casually. Therefore, in the embodiment, the medical waste is subject to a vacuum compression treatment, and then the medical waste is temporarily stored in the storage part, so that the ultrasound-guided interventional operation vehicle may simultaneously store the medical waste after a plurality of interventional operations, and may return to the hospital to uniformly treat the medical waste after one outgoing journey is finished.

The present disclosure is described in detail above in combination with the accompanying drawings and embodiments. However, the present disclosure is not limited to the above-mentioned embodiments, and various changes may be made within the knowledge of those skilled in the art without departing from the gist of the present disclosure. The contents not described in detail in the present disclosure may adopt the prior art.

What is claimed is:

1. A vehicle designed for ultrasound-guided interventional operation, comprising:
    a vehicle body, wherein the vehicle body is provided with a carriage;
    an operating table arranged in the carriage;
    an operating lamp arranged in the carriage;
    an ultrasonic device arranged in the carriage, wherein the ultrasonic device is configured to provide the ultrasonic guidance;
    a monitoring device arranged in the carriage, wherein the monitoring device is configured to monitor vital signs of patients during an operation procedure;
    an anesthesia device arranged in the carriage, wherein the anesthesia device is configured to maintain an anesthesia state of the patient during the operation procedure; and
    a fixing device arranged on an inner wall of the carriage, wherein the fixing device is configured to fix the ultrasonic device, the monitoring device and the anesthesia device with the inner wall of the carriage during a driving process of the vehicle body.

2. The ultrasound-guided interventional operation vehicle according to claim 1, wherein the fixing device comprises:
    a plurality of fixing pieces, wherein each of the fixing pieces corresponds to a to-be-fixed device.

3. The ultrasound-guided interventional operation vehicle according to claim 2, wherein each of the fixing pieces comprises:
    a first fixing part and a second fixing part, wherein the first fixing part and the second fixing part are arranged on an inner side wall of the carriage; and
    a fixing belt, wherein two ends of the fixing belt are respectively connected with the first fixing part and the second fixing part, and the fixing belt enables the to-be-fixed device to be fixed in an accommodation space formed between the fixing belt and the inner side wall of the carriage.

4. The ultrasound-guided interventional operation vehicle according to claim 3, wherein each of the fixing pieces further comprises:
    an accommodating part rotatably arranged in the first fixing part, wherein an end portion of the fixing belt is fixedly connected with the accommodating part, and when the accommodating part rotates, the fixing belt is enabled to be accommodated in the first fixing part or released from the first fixing part.

5. The ultrasound-guided interventional operation vehicle according to claim 4, wherein each of the fixing pieces further comprises:
    a stopping part connected with the accommodating part, wherein the stopping part is enabled to limit a rotation of the accommodating part.

6. The ultrasound-guided interventional operation vehicle according to claim 5, wherein the stopping part is configured to automatically restrict the rotation of the accommodating part when the fixing belt is subjected to a force greater than a preset value.

7. The ultrasound-guided interventional operation vehicle according to claim 3, wherein the fixing device further comprises:
    a guide rail arranged on the inner side wall of the carriage, wherein the first fixing part and the second fixing part are slidably connected with the guide rail.

8. The ultrasound-guided interventional operation vehicle according to claim 7, wherein the fixing device comprises a plurality of guide rails, and the plurality of guide rails are arranged at different heights of the inner side wall of the carriage.

9. The ultrasound-guided interventional operation vehicle according to claim 1, wherein the operating lamp comprises:
    a telescopic part slidably connected with a top plate of the carriage and extending towards a bottom plate of the carriage; and
    a lamp cap rotatably arranged at an end of the telescopic part close to the bottom plate of the carriage.

10. The ultrasound-guided interventional operation vehicle according to claim 9, wherein the top plate of the carriage is provided with a chute, and an end of the telescopic part is slidably arranged in the chute.

11. The ultrasound-guided interventional operation vehicle according to claim 10, wherein the top plate of the carriage is provided with a plurality of chutes, which are arranged radially, and the telescopic part is slidable in any one of the chutes.

12. The ultrasound-guided interventional operation vehicle according to claim 10, wherein the chute comprises a circular chute and a plurality of linear chutes, moreover the plurality of linear chutes are connected with the circular chute and arranged radially around the circular chute, and the telescopic part is slidable in the circular chute or any one of the linear chutes.

13. The ultrasound-guided interventional operation vehicle according to claim 1, wherein the vehicle comprises:
    a main carriage; and
    at least one expansion carriage, wherein the expansion carriage is slidably connected with a side wall of the main carriage, so that the expansion carriage is enabled to be accommodated in the main carriage or slid out of the main carriage to expand a space.

14. The ultrasound-guided interventional operation vehicle according to claim 13, wherein each expansion carriage comprises:
    a side plate slidably connected with the side wall of the main carriage; and
    a main plate rotatably connected with the side plate, wherein when the expansion carriage is accommodated the main carriage, the side plate is fitted with an inner surface of the side wall of the main carriage,
    wherein a joint between the side plate and the main carriage is provided with a sealing strip.

15. The ultrasound-guided interventional operation vehicle according to claim 1, further comprising:

a transfer door arranged at a rear of the carriage;

a transfer ladder arranged at the rear of the carriage and rotatably connected with a bottom plate of the carriage.

16. The ultrasound-guided interventional operation vehicle according to claim 15, wherein the transfer ladder comprises:

a plate body, wherein an end of the plate body is rotatably connected with the bottom plate of the carriage;

a track covered on a surface of the plate body; and a driving part configured to drive the track to slide relative to the plate body.

17. The ultrasound-guided interventional operation vehicle according to claim 15, wherein the transfer ladder comprises:

a plate body, wherein an end of the plate body is rotatably connected with the bottom plate of the carriage; and a hydraulic supporting part arranged at an end of the plate body away from the carriage.

18. The ultrasound-guided interventional operation vehicle according to claim 15, wherein the carriage is provided with an isolation door and an isolation plate, the isolation door, the isolation plate and a side wall of the carriage jointly prescribe a limit to an operating room, and the isolation door is arranged on a side close to the rear of the carriage.

19. The ultrasound-guided interventional operation vehicle according to claim 18, further comprising:

an air purification device configured to purify air in the operating room, wherein the air purification device comprises:

an air purifier arranged on a side of the isolation plate away from the operating room;

an air duct connected with the air purifier, wherein the air duct passes through the isolation plate and extends at a top of the operating room; and a plurality of air outlets arranged on a side of the air duct facing a bottom of the operating room.

20. The ultrasound-guided interventional operation vehicle according to claim 18, further comprising:

a waste treatment device arranged on a side of the isolation door away from the operating room, wherein the waste treatment device comprises:

a vacuum compression part configured to perform a vacuum and compression treatment on a medical waste; and a storage part configured to store the medical waste after treatment.

* * * * *